(12) United States Patent
Khalaj

(10) Patent No.: US 6,247,997 B1
(45) Date of Patent: Jun. 19, 2001

(54) ABRASIVE CLEANING SYSTEM

(76) Inventor: Ben M. Khalaj, 4 Autry, Irvine, CA (US) 92618

( * ) Notice: Subject to any disclaimer, the term of this patent is extended or adjusted under 35 U.S.C. 154(b) by 0 days.

(21) Appl. No.: 09/407,591

(22) Filed: Sep. 28, 1999

(51) Int. Cl.[7] ........................................ B24C 3/00
(52) U.S. Cl. ........................................................... 451/2
(58) Field of Search ........................... 451/2, 5, 75, 87, 451/89, 90, 91

(56) References Cited

U.S. PATENT DOCUMENTS

| | | | |
|---|---|---|---|
| 4,232,487 | * 11/1980 | Brown | 451/90 |
| 4,333,277 | * 6/1982 | Tasedan | 451/88 |
| 4,375,740 | * 3/1983 | Brown | 451/90 |
| 4,671,022 | * 6/1987 | Williams | 451/2 |
| 5,279,075 | * 1/1994 | Sage et al. | 451/2 |
| 5,545,074 | * 8/1996 | Jacobs | 451/40 |
| 5,971,999 | * 10/1999 | Naldoni | 606/131 |

* cited by examiner

Primary Examiner—Joseph J. Hail, III
Assistant Examiner—David B. Thomas

(57) ABSTRACT

An abrasive cleaning system that utilizes a central vacuum compressor, at least one in-line filtration device and at least one control panel unit to be placed in a treatment station. This system has an option to expand by adding two or more additional control panel units in two or more treatment stations. The number of these add on control panel units depends upon the design layout of the system unit which can be unlimited.

7 Claims, 5 Drawing Sheets

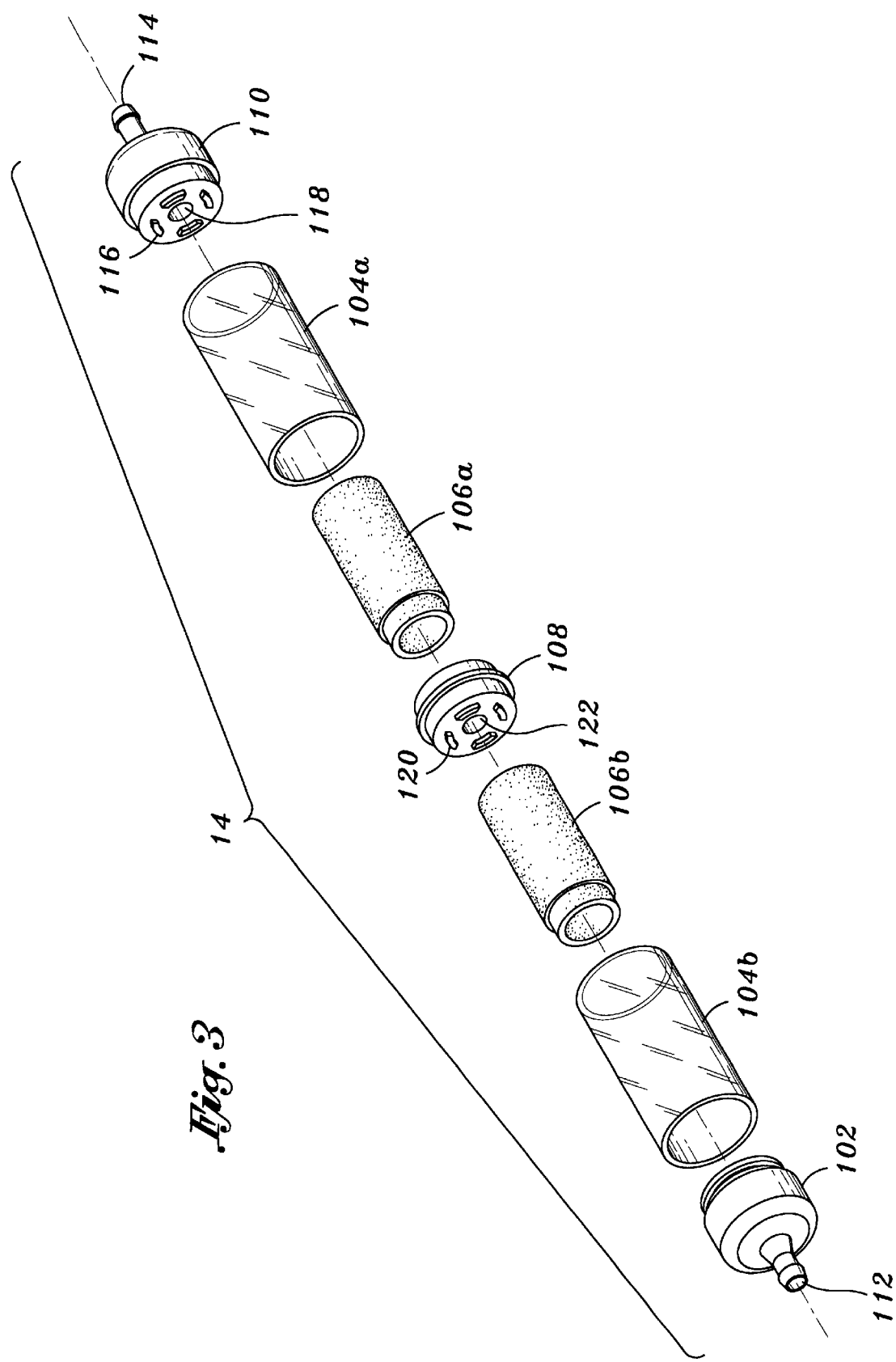

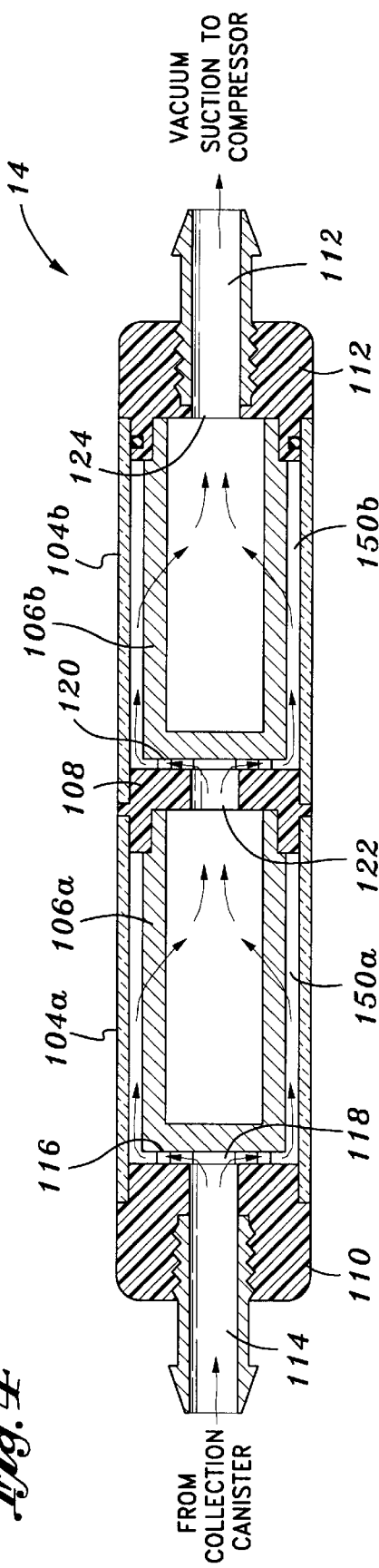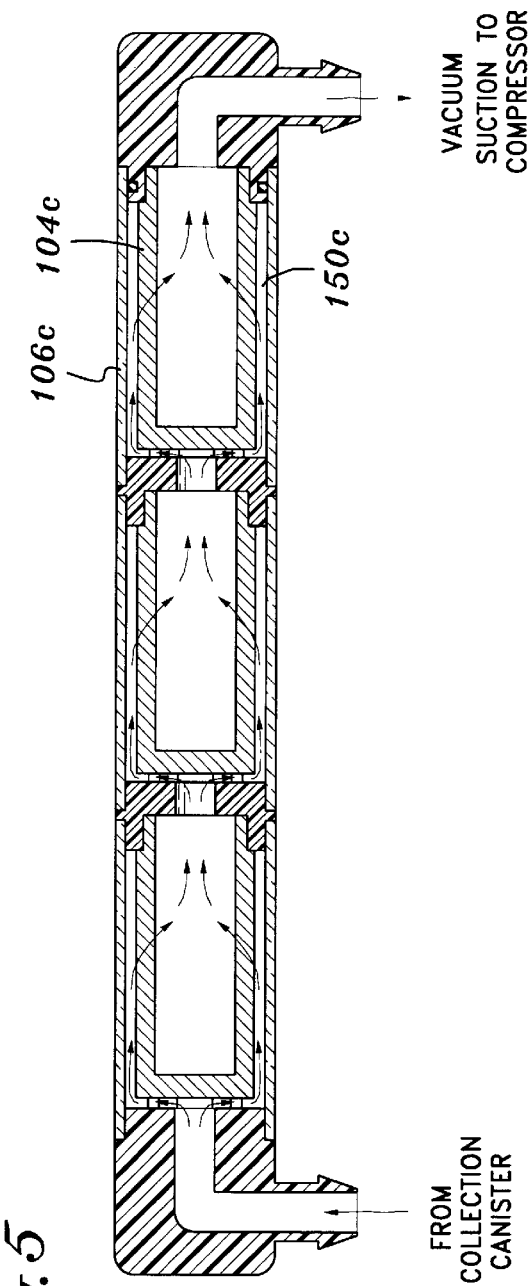

ABRASIVE CLEANING SYSTEM

FIELD OF THE INVENTION

The present invention relates to abrasive cleaning devices that can remove and capture dirt and debris from a surface by using abrasive particles with mixture of high pressurized air and vacuum. More particularly, the invention relates to an abrasive-cleaning device utilizing a system having a central vacuum compressor with plurality of control panel units that can be placed in treatment stations to be used for unlimited number of users.

BACKGROUND OF THE INVENTION

Abrasive cleaning devices are well known as surfacing applicators to treat surfaces for cleaning, smoothing, etching and resurfacing a damaged area such as human skin. These devices operate on a high stream of a pressurized air or vacuum suction to carry abrasive particles to be impinged against the surface. The high pressures of abrasive particles removes dirt and debris from a surface and provides an extremely satisfactory cleaning means.

In spite of the advantages of these devices in prior art, there are some disadvantages and limitations that can not be delivered for the purpose of productivity. For example, only one operator at a time can use this device while using the applicator to treat a patient. The usage of the unit is entirely limited to a sole operator. In case of needing another operator for more productivity, additional unit must be purchased and that is not a cost-effective approach.

Another disadvantage of the prior art unit is that the vacuum compressor is built in with control panel and while the unit is operating, the compressor makes a loud noise and generates heat in the treatment room and it's very inconvenient. However, this invention overcomes the shortcomings of conventional units and provides a system that utilizes a central vacuum compressor with an option to expand the system and provide additional treatment stations for unlimited number of operators at very lower cost and achieve maximum productivity.

SUMMARY OF THE INVENTION

It is an object of the present invention to provide an improved abrasive cleaning system that utilizes a central vacuum compressor, at least one in-line filtration device and at least one control panel unit to be placed in a treatment station. Said compressor is placed in a separate room away from treatment stations to eliminate the compressor noise in treatment stations.

It is also an object of this invention to expand the system by adding two or more additional control panel units to the original system set up. The number of these additional control panel units depends upon the design layout of the system unit, which can be unlimited. Therefore by expanding the system unit, we can provide multi-treatment stations at very low cost to treat patients and to be productive.

In each treatment station, a control panel unit may be a wall mounted panel or a tabletop panel that includes a handpiece, a collection canister, a source canister, a vacuum adjustment knob and a control flow knob to adjust the flow of the abrasive particles. The in-line filtration device may also be included in this unit.

It is another object of this invention to provide in-line filtration device with this system to collectively capture particles and optionally be able to expand the filtration device with additional filters. It is preferable to have straight type fitting connections to the system to eliminate any loss of vacuum flow in 90 degrees angle and retain maximum vacuum source. However, the elbow connection fitting may be used in some system configurations for purpose of controlling the vacuum flow. Said in-line filtration device includes a least two proxy-filters connected at each end with a connecting part with a passage of flow between the two filters, two end caps with hose fittings connectors, and at least one translucent cover.

Further objects and advantages of this invention will become apparent from consideration of the drawings and description that follows.

BRIEF DESCRIPTION OF THE DRAWINGS

Exemplary embodiments of the invention will now be described in conjunction with the drawings in which:

FIG. 3 is an exploded view of the in-line filtration device.

FIG. 4 is a cross sectional view taken along line 4—4 in FIG. 1.

FIG. 5 is a cross sectional view similar to FIG. 4 except an additional filter has been added and the caps are modified.

DETAILED DESCRIPTION OF THE INVENTION

Figure 1:
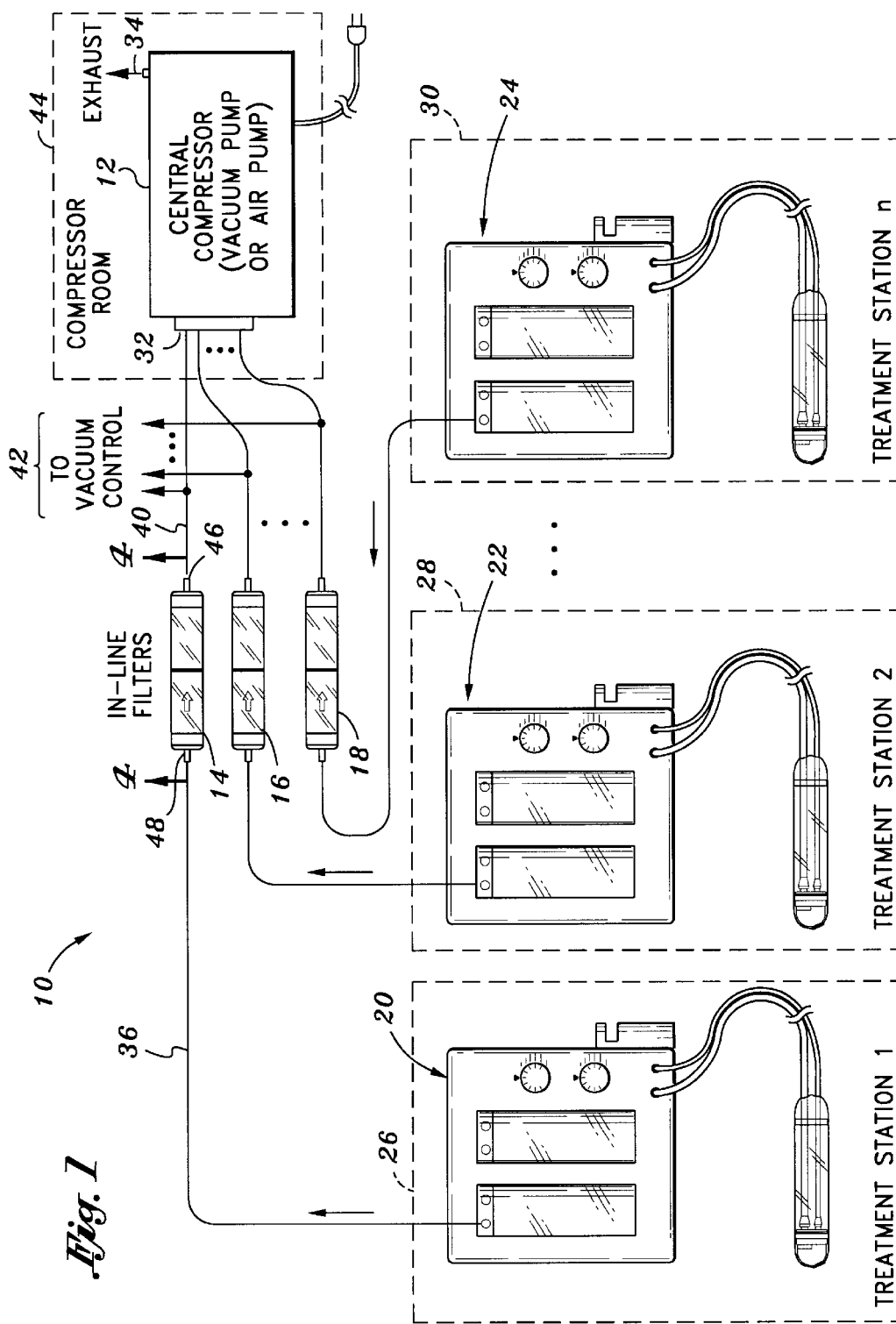
FIG. 1 is a block diagram of the present invention showing a system unit in conjunction with multi-treatment stations.

FIG. 1 is showing an abrasive cleaning device 10 that utilizes a system that includes a central compressor 12, an arrangement of at least one in-line filtration device 12, an arrangement of at least one control panel unit 20 located in a treatment station 26. The central compressor unit 12 has a number of vacuum ports 32 and an exhaust port 34. Vacuum ports 34 may be connected to a manifold to distribute a vacuum suction from a central compressor 12.

The compressor 12 at its vacuum port 32 is connected by a vacuum hose 40 to at least one in-line filtration device 14 at its outlet port 46. The filtration device 14 is to capture sand type particles, So that the compressor runs smoothly and last longer. At the other end of the in-line filtration device 14 at its inlet port 48, a connecting hose 36 is connected to control panel unit 20.

Preferably, the compressor 12 separated from the control panel unit 20, and it is located in a compressor room 44 to eliminate the noise extracted by the compressor 12 in a treatment station 26 where the patient is being treated for a medical procedure.

FIG. 1 is also illustrates the system unit in a basic and in comprehensive configuration. The basic configuration is designed for one treatment station 26 and can be expanded for two or more treatment stations 28, 30 for comprehensive configuration that accommodate two or more control panel units 22, 24 with possible two or more in-line filtration devices 16 and 18 using a central compressor 12. This type of system unit has advantages over the prior art devices, because the system is expandable and cost-effective.

Figure 2A:
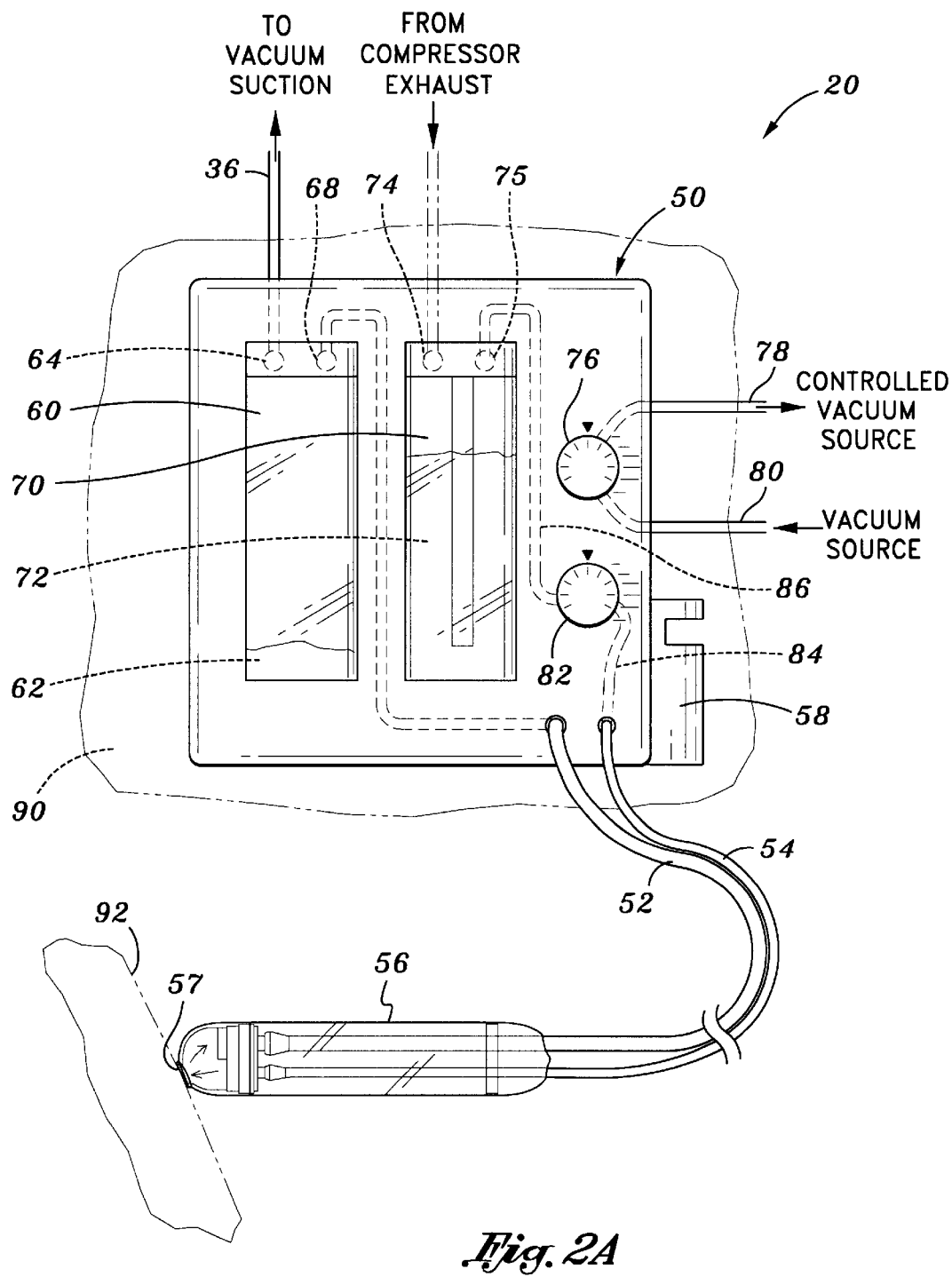
FIG. 2A is a partial view of a control panel unit shown as a wall mount panel for each treatment station.
Figure 2B:
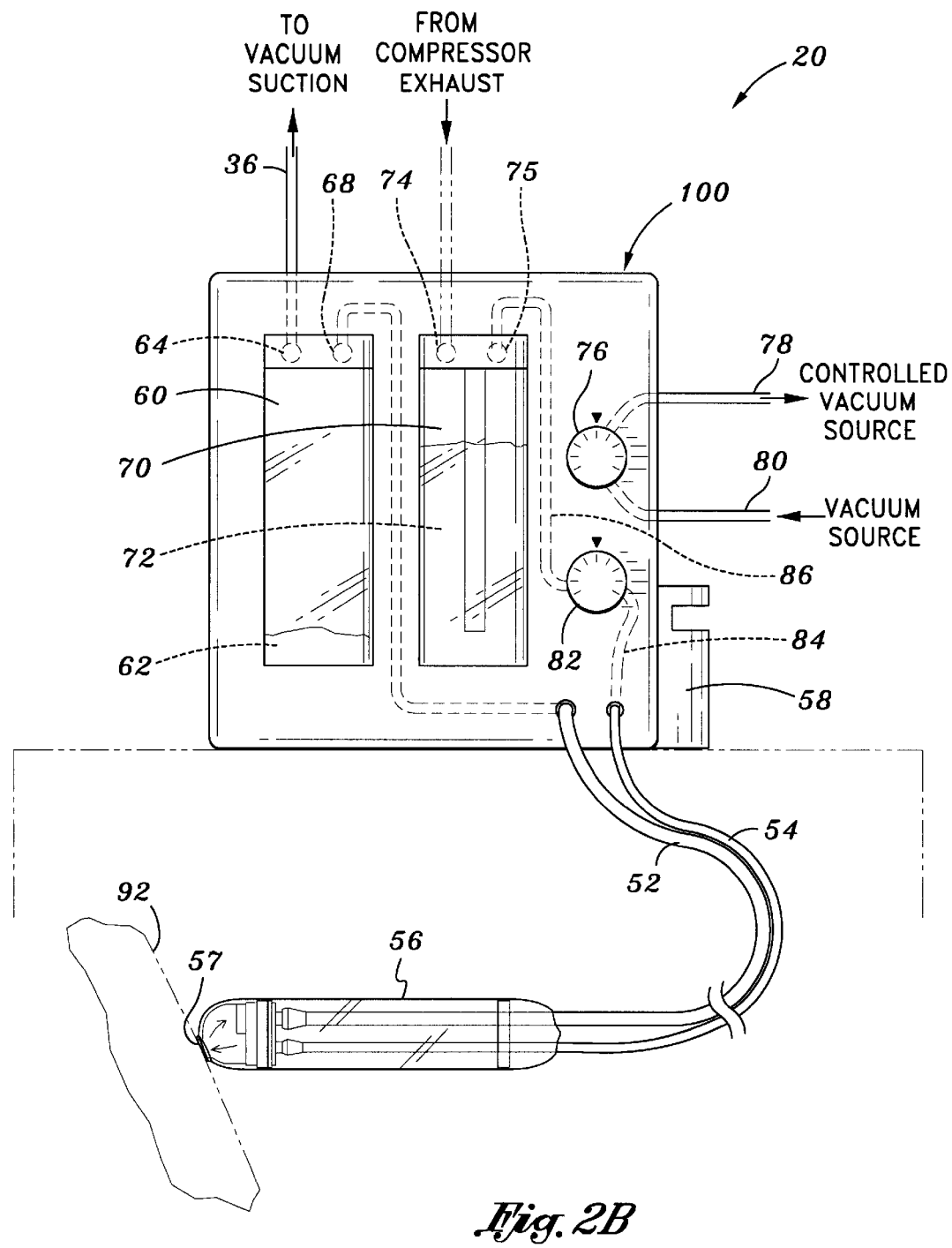
FIG. 2B is a partial view of a control panel unit shown as a tabletop panel for each treatment station.

Referring to FIGS. 2A and 2B, showing a control panel unit 20 that can be a wall mounted panel 50 or a table top panel 100. The control panel unit 20 includes a handpiece 56, a collection canister 60, a source canister 70 that contains abrasive particles, a vacuum adjustment knob 76 to control and adjust the vacuum source from the central compressor 12, a control flow knob to adjust the flow of the abrasive particles from a source canister to the handpiece. This control panel unit 20 may also include the in-line filtration device 14 as part of this assembly.

The applied vacuum suction from the central compressor 12, that is directed to the outlet port 64 of collection canister 60 activates the circulation of abrasive particle 72 in source canister 70 at its outlet port 75 to the handpiece 56 through a control flow knob 82 and a pair of vacuum tubes 52, 54. The handpiece 56 eject a mixture of high pressurized air with stream of abrasive particles at its tip 57 onto a surface 92 for cleaning means to remove the debris from the surface 92. The pressure flow from the compressor exhaust may also be use in this control panel unit to circulate the abrasive particles 72 within the source canister 70 to provide better circulation of the abrasive particles in the system.

Another important device in this system unit is the in-line filtration device 14 as shown in FIG. 3 and FIG. 4. This device comprises at least two filters 106a and 106b preferably proxy type filters, a connecting part 108 to connect or position the filters 106a and 106b at its end, two end caps 102, 110 with connector fitting 114, 112 preferably straight connector, and at least one translucent cover 104 to cover the filters 106a, 106b and the connecting part 108 to be assemble with the end caps 102, 110. Through the vacuum suction flow that is generated by the compressor, the in-line filtration device filters the abrasive particles. The flow passes through the inlet port 114 and move on to first filter 106a. The end cap 110 has a number of projected tabs 116 that is abut with the end of the first filter. The vacuum suction flow passes through the opening created by these projected tabs 116 and forwarded to the chamber 150a between the first filter 106a and cover 104a. Some of the particles are capture by the first filter and the remaining particles move on to the second chamber 150b between the second filter 106b and the cover 104b to be capture completely. The connecting part 108 is positioned between the first filter 106a and the second filter 106b. This connecting part includes a number of projected tabs 120 for flow of vacuum suction to the second filter 106b and it also has a central opening 122.

The in-line filtration device 14 can be modifying for more than two filters as shown in FIG. 5. Additional filter 106c can be added to this device for better filtration to meet the system requirement for cleaner flow.

While this invention is susceptible of embodiments in many different forms, this specification and the accompanying drawings disclose only some specific forms as examples of the invention. The invention is not intended to be limited to the embodiments so described, however, the scope of the invention is pointed out in the appended claims

I claim:

1. An abrasive cleaning system in conjunction with treatment stations for multi-users, comprising:

a central vacuum compressor, said compressor having number of vacuum suction ports and an exhaust port;

a plurality of control panel units, said control panel units operates in conjunction with said central compressor, said each control panel unit includes a handpiece, a collection canister, a source canister, a vacuum adjustment knob to control and adjust the vacuum source from said compressor to said control panel, and a control flow knob to adjust the flow of the abrasive particles from said source canister to said handpiece, said collection canister is also connected to vacuum source of said compressor; and;

at least one in-line filtration device, said in-line filtration device having an outlet port and an inlet port, said inlet port connected to said compressor vacuum ports and said outlet ports connected to at least one said control panel unit.

2. An abrasive cleaning system according to claim 1, wherein said a central vacuum compressor is placed in a separate room away from treatment stations.

3. An abrasive cleaning system according to claim 1, wherein said control panel unit is a wall mount panel configuration.

4. An abrasive cleaning system according to claim 1, wherein said control panel unit is a table top panel configuration.

5. An abrasive cleaning system according to claim 1, wherein said in-line filtration device includes an arrangement of a least two in-line filters connected at each end to a connecting part, said connecting part provides flow passage of vacuum source and filtration of abrasive particles between two said in-line filters, two end caps with inlet port and outlet port fittings connected to the other end of said in-line filters, and at least one translucent cover to enclosed assembly of said in-line filters, said connecting part and said end caps.

6. An abrasive cleaning system in conjunction with treatment stations for multi-users, comprising:

a central vacuum compressor, said compressor having number of vacuum suction ports and an exhaust port, and;

a plurality of control panel units, said control panel units operates in conjunction with said central compressor, said each control panel unit includes a handpiece, a collection canister, a source canister, in-line filtration device, a vacuum adjustment knob to control and adjust the vacuum source from said compressor to said control panel, and a control flow knob to adjust the flow of the abrasive particles from said source canister to said handpiece, said collection canister is also connected to vacuum source of said compressor.

7. An abrasive cleaning system according to claim 6, wherein said a central vacuum compressor is placed in a separate room away from treatment stations.

* * * * *